(12) United States Patent
Lehto et al.

(10) Patent No.: US 8,282,616 B2
(45) Date of Patent: Oct. 9, 2012

(54) PANT-TYPE ABSORBENT ARTICLE AND A METHOD FOR PRODUCING PANT-TYPE ABSORBENT ARTICLES

(75) Inventors: Marcus Lehto, Fotö (SE); Lars Melin, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 382 days.

(21) Appl. No.: 12/518,774

(22) PCT Filed: Dec. 22, 2006

(86) PCT No.: PCT/SE2006/001501
§ 371 (c)(1),
(2), (4) Date: Jun. 11, 2009

(87) PCT Pub. No.: WO2008/079061
PCT Pub. Date: Jul. 3, 2008

(65) Prior Publication Data
US 2010/0063468 A1 Mar. 11, 2010

(51) Int. Cl.
*A61F 13/496* (2006.01)
(52) U.S. Cl. ............... 604/385.3; 604/366; 604/385.01; 604/385.21; 604/394; 604/396
(58) Field of Classification Search ............... 604/394, 604/395, 396, 385.01, 370, 371, 366, 392
See application file for complete search history.

(56) References Cited

U.S. PATENT DOCUMENTS

| | | | |
|---|---|---|---|
| 5,143,679 A | 9/1992 | Weber et al. | |
| 5,156,793 A | 10/1992 | Buell et al. | |
| 5,167,897 A | 12/1992 | Weber et al. | |
| 5,422,172 A | 6/1995 | Wu | |
| 5,569,234 A | 10/1996 | Buell et al. | |

(Continued)

FOREIGN PATENT DOCUMENTS

EP 0 625 346 A1 11/1994

(Continued)

OTHER PUBLICATIONS

PCT/ISA/210 completed Aug. 2, 2007.

(Continued)

*Primary Examiner* — Loan Thanh
*Assistant Examiner* — Peter S Vasat
(74) *Attorney, Agent, or Firm* — Buchanan Ingersoll & Rooney PC (57) ABSTRACT

A pant-type absorbent article including a chassis structure including a front panel having a front end edge and first and second side edges, a back panel having a back end edge and first and second side edges and a crotch panel arranged between the front and back panels at least one of said front and back panels including an elastic nonwoven/film laminate, and a core being integrated with the chassis structure, the first and second side edges of the front panel being joined by side seams to the corresponding first and second side edges of the back panel. Each side seam is formed at least in part in a weldable connecting member, the connecting member including a first part being secured to a side edge on the front panel and a second part being secured to a corresponding side edge on the back panel, said first and second parts of said connecting member being joined by thermowelding to form said side seam.

28 Claims, 4 Drawing Sheets

U.S. PATENT DOCUMENTS

| | | | |
|---|---|---|---|
| 5,592,160 A | | 1/1997 | Bennett et al. |
| 5,592,690 A | | 1/1997 | Wu |
| 5,628,738 A | * | 5/1997 | Suekane ............... 604/385.26 |
| 5,634,216 A | | 6/1997 | Wu |
| 5,733,628 A | | 3/1998 | Pelkie |
| 5,861,019 A | | 1/1999 | Sun et al. |
| 5,861,074 A | | 1/1999 | Wu |
| 2002/0138063 A1 | * | 9/2002 | Kuen et al. ............... 604/391 |
| 2003/0018315 A1 | * | 1/2003 | Popp et al. ............... 604/386 |
| 2003/0105447 A1 | * | 6/2003 | Widlund et al. ......... 604/385.28 |
| 2003/0120254 A1 | * | 6/2003 | Franke et al. ............. 604/396 |
| 2003/0135184 A1 | | 7/2003 | Van Gompel et al. |
| 2004/0034327 A1 | | 2/2004 | Kuen et al. |
| 2004/0102757 A1 | | 5/2004 | Olson |
| 2005/0113793 A1 | * | 5/2005 | Bianco ..................... 604/391 |
| 2006/0042746 A1 | | 3/2006 | Ukegawa |
| 2006/0212019 A1 | | 9/2006 | Otsubo et al. |
| 2006/0271009 A1 | | 11/2006 | Cartier et al. |
| 2006/0282058 A1 | | 12/2006 | Otsubo et al. |

FOREIGN PATENT DOCUMENTS

| | | |
|---|---|---|
| GB | 2 257 652 A | 1/1993 |
| JP | 2001-129016 A | 5/2001 |
| JP | 2005-533529 A | 11/2005 |
| JP | 2006-255191 A | 9/2006 |
| JP | 2008-531181 A | 8/2008 |
| JP | 2009-538165 A | 11/2009 |
| WO | WO 03/041988 A1 | 5/2003 |
| WO | WO 03/047488 A1 | 6/2003 |
| WO | WO 03/057116 A1 | 7/2003 |
| WO | WO 2005/122984 A1 | 12/2005 |
| WO | WO 2005/122985 A1 | 12/2005 |
| WO | WO 2006/093444 A1 | 9/2006 |
| WO | WO 2007/138373 A1 | 12/2007 |

OTHER PUBLICATIONS

PCT/ISA/237 completed Aug. 2, 2007.

English version of an Office Action (Notice of Reasons for Rejection) issued on Nov. 29, 2011, in corresponding Japanese Patent Application No. 2009-542696.

Extended European Search Report (Supplementary European Search Report and European Search Opinion) issued Mar. 15, 2012, in corresponding EP Application No. 06835909.0, 8 pages, European Patent Office, Munich, DE.

* cited by examiner

PANT-TYPE ABSORBENT ARTICLE AND A METHOD FOR PRODUCING PANT-TYPE ABSORBENT ARTICLES

TECHNICAL FIELD

The invention pertains to a pant-type absorbent article comprising a chassis structure comprising a front panel having a front end edge and first and second side edges, a back panel having a back end edge and first and second side edges and a crotch panel arranged between the front and back panels and a core component being integrated with the chassis structure, the first and second side edges of the front panel being joined by side seams to the corresponding first and second side edges of the back panel.

BACKGROUND ART

Pant-type absorbent articles commonly include a pant-shaped chassis structure and an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is also desirable that the articles are capable of being pulled up and down over the hips of the wearer in the manner of a pair of underpants to allow the wearer or caregiver to easily remove a soiled article and to replace it with a new clean article. For these reasons, the article chassis is usually made of a material that is elastically stretchable, at least around the waist and in the areas intended to be applied over the wearer's hips.

Traditionally, the chassis of pant-type absorbent articles have been made from layers of non-elastic thermoplastic nonwoven material having elastic elements such as threads or bands arranged between the layers to elasticise selected portions of the chassis. In these articles, the fibres and bonds of the nonwoven webs remain unbroken during the production of the chassis structure and can be used to form strong and yet openable welds and seams between the chassis parts. However, in order to meet the demand for more underwear-like pant-type articles, the traditional elastification by means of elastic elements has been replaced by elastic nonwoven/film laminates.

One example of an elastic laminate for use in pant-type absorbent articles is disclosed in WO 03/041988. The laminate is composed of an elastic film applied between two nonwoven layers. During production of the elastic laminate, the nonwoven layers have been bonded to the film after which the laminate has been subjected to activation treatment involving incremental stretching of the laminate that causes bonds and fibres in the nonwoven webs to break. As a result, the elasticity of the activated laminate is largely the same as the elasticity of the elastic film. A problem with activated nonwoven/film laminates of this type is that welded seams formed in the mechanically weakened materials have poor tensile strength. This means that there is a risk that the seams will break prematurely when the pant-type article is put on a wearer or when it is being worn.

Other examples of elastic laminates used in the construction of pant-type articles are disclosed in WO 2005/122984 and WO 2005/122985. The materials in these applications differ from that disclosed in WO 03/041988 in that the bonds and fibres of at least one nonwoven layer in the elastic laminate have not been completely broken. Instead, the layer retains some residual strength. PCT applications WO 2005/122984 and WO 2005/122985 describe laminates in which elasticity has been combined with softness and resistance to puncture of the laminates. However, welded side seams in pant-type articles comprising such laminates still show low tensile strength when compared to the weld seams of traditional pants made of nonwoven layers that have been elasticised by means of elastic threads or bands.

The pant-type absorbent articles are usually formed with seams or joins at the sides of the chassis structure to connect the article's front portion to the rear portion and to form a pant having a waist opening and leg openings. Normally, the side joins are arranged so that they will be placed at the user's hips during use of the absorbent pants, but it is also known to arrange side joins more to the front of the article.

The side-seams are preferably made such that they will provide sufficient integrity to the chassis while it is being put on and while it is being worn. This means that the side-seams should withstand the tensile stress arising when the pant-type article is pulled up over the wearer's hips and also any stress that may occur at the side seams as a result of the wearer's movements during use of the article. However, it has proven to be a great advantage if the side-seams can be broken apart in a controlled manner after use of the article so that a soiled article can be easily removed from the user without having to be pulled down along the legs. Openable side-seams are most readily formed by welding techniques such as ultrasonic welding or thermowelding of thermoplastic components in the chassis material. A problem with the elastic laminate materials used for creating an elastic chassis structure is that they generally have poor weldability, resulting in weak side seams that will fail when putting on the article or when the article is being worn.

Accordingly, it is an object of the invention to provide an elastic pant-type absorbent article comprising elastic laminate materials and showing sufficient strength to withstand the forces arising when putting on and wearing the article.

It is also an object of the invention to offer an elastic pant-type absorbent article comprising elastic laminate materials and having openable side seams.

A further object of the invention is to provide a simple and efficient method for producing an elastic pant-type absorbent article having side seams showing sufficient strength to withstand the forces arising when putting on and wearing the article.

DISCLOSURE OF THE INVENTION

In accordance with the invention, there is offered a pant-type absorbent article comprising a chassis structure comprising a front panel having a front end edge and first and second side edges, a back panel having a back end edge and first and second side edges and a crotch panel arranged between the front and back panels at least one of said front and back panels comprising an elastic nonwoven/film laminate, and a core being integrated with the chassis structure, the first and second side edges of the front panel being joined by side seams to the corresponding first and second side edges of the back panel, wherein each said side seam is formed in a weldable connecting member, the connecting member comprising a first part being secured to a side edge on the front panel and a second part being secured to a corresponding side edge on the back panel, said first and second parts of said connecting member being joined by thermowelding to form said side seam.

In order to create a strong shearing bond between the connecting member and the front and back panel of the chassis structure, the connecting member may be permanently secured to the front and back panels. By a permanent securement is implied that the join between the materials is so strong that the material outside the join will break before or at the same time as the join breaks under tensile stress.

The connecting member may be secured to the front and back panels by means of an adhesive. Suitable adhesives are thermoplastic hotmelt adhesives or latex with hotmelt adhesives being particularly preferred. The adhesive may be applied as a full coating, in a pattern such as a dot pattern or line pattern and by any suitable method such as by spraying, nozzle coating, printing, etc. However, other securement methods may be used such as thermal or ultrasonic welding.

The bond between the connecting member and each of the front and back panels is made within an overlapping area of the connecting member and the chassis panel. In this manner, the connecting member will serve to connect the front and back panels by being attached to the often relatively weak elastic laminate material in these panels by a bond occupying a comparatively large area, in the order of from 200 mm$^2$ to 60000 mm$^2$, that will only be exposed to shearing stress and not to the peeling forces arising at the side seams during normal use of the article. Accordingly, the connecting member serves as a reinforcement of the chassis panel material at the side edges of the absorbent article and also provides a weldable material for creating a strong, preferably openable, welded side seam.

The side joins are preferably openable side joins, implying that they are sufficiently strong to withstand stress during donning and wearing of the pant-type absorbent article but that they can be peeled or torn apart in a controlled manner when removing the article after use. Preferably, the side joins can be opened in the welded side seams. However, it is also conceivable to make the join between the connecting member and the front panel openable and optionally reclosable.

The connecting member is a thermoweldable component. Hence, the connecting member can be welded by means of any method involving heating and softening or melting of the material, such as bonding by heated tools, mechanical compressive heat generating bonding (pressure bonding), or ultrasonical bonding. In order to be thermoweldable, the connecting member should comprise a sufficient amount of thermoplastic material. Examples of suitable thermoplastic polymers for use in the connecting member are polyethylene, polyesters, polypropylene and other polyolefin homopolymers and copolymers and blends of thermoplastic polymers. The connecting member may comprise a thermoplastic film or a thermoplastic nonwoven web or a laminate of two or more layers of film or nonwoven. Particularly well suited nonwoven webs are those comprising thermoplastic fibres that are a blend of polypropylene and polyethylene fibres. The weldable nonwoven webs and films have a high content of thermoplastic material and contain at least 50% thermoplastic material and preferably at least 80% thermoplastic material.

According to a preferred embodiment of the invention, the connecting member consists of two rectangular pieces of material that have been joined along a common edge while being placed in direct face-to-face relationship. In this embodiment, the connecting member is a rectangular piece of material having a welded join running across the piece of material, preferably parallel to the side edges of the front and back panels on the chassis structure and forming the side join on the pant-type absorbent article.

The rectangular connecting member may have a width perpendicular to the side seam of 20-200 mm. The width of the connecting member determines the overlap between the connecting member and the material in the front and back panels. For small-size articles, such as diapers for prematurely born babies, it may be sufficient with an overlap of 10 mm in order to provide sufficient area for a reliable bond. However, for large-size articles intended for use by heavily incontinent adults, it may be necessary to have an overlap of up to 100 mm.

The connecting member may have a length parallel to the side seam corresponding to at least 25% of the length of the side seam. Accordingly, the connecting member may be arranged to provide only a part of the side seam between the waist opening of the article and the leg openings. Typically, the connecting member may be arranged only along those parts of the respective side edges of the front and back panels that are made of materials having poor weldability, such as elastic laminates being part of the chassis structure of the pant-type article. If the pant-type absorbent article is provided with an elastic waist panel, the waist panel may include layers of weldable material such as non-elastic nonwoven material. However, in order to fully benefit from the production advantages provided by producing the connecting members and the welded seams separately, the connecting members are preferably arranged so that they provide the total length of the side seams. In that way, the welding step can be made independently from the high-speed main production process for the pant-type article and the pre-fabricated connecting members can be introduced into the high-speed pant production process without regard to the comparatively low-speed welding step.

The pant-type absorbent article according to the invention may be provided with an elastic waist panel that is arranged on at least one of the front and back panels. The elastic waist panel may extend continuously all the way between the side joins and may completely encircle the waist opening of the absorbent article.

The absorption core may be a component that is incorporated into the chassis structure separately or as a part of a core component or "core pack" comprising a topsheet, a barrier sheet and the absorption core arranged between the topsheet and the barrier sheet.

The invention also provides a method for producing a pant-type absorbent article each article including a chassis structure comprising a front panel having a front end edge and first and second side edges, a back panel having a back end edge and first and second side edges and a crotch panel arranged between the front and back panels said chassis structure having an integrated absorbent core component, the method including a pant-forming process comprising forming the chassis structure and joining the first and second side edges of the front panel to the corresponding first and second side edges of the back panel, and incorporating the absorbent core component into the chassis structure.

In accordance with the invention, the pant-forming process comprises the following additional steps:
 a) producing a continuous web of connecting member blanks by joining two continuous webs of weldable material in face-to-face relationship along paired weld lines extending transversely across the web of connecting member blanks;
 b) severing the web of connecting member blanks between each pair of weld lines to create individual connecting member blanks;
 c) securing said individual connecting member blanks to a chassis web at predetermined locations along a first edge of said chassis web with said weld lines arranged in the transverse direction of the chassis web;
 d) folding said chassis web along a longitudinal folding line to bring a second edge of said chassis web in alignment with said first edge of said chassis web;

e) securing said chassis web to said connecting member blanks along said second edge of said chassis web;

f) severing said chassis web between said weld lines in said connecting member blanks to separate individual pant-type articles from said chassis web.

The connecting member blanks can be permanently secured to the chassis web in step c) and/or in step e).

The method according to the invention may further include any conventional pant-forming production steps such as cutting the chassis web to form leg openings, attaching elastic elements at the leg and waist openings, etc.

BRIEF DESCRIPTION OF DRAWINGS

The invention will in the following be described in greater detail with reference to the appended drawings, wherein.

EMBODIMENTS OF THE INVENTION

Figure 1:
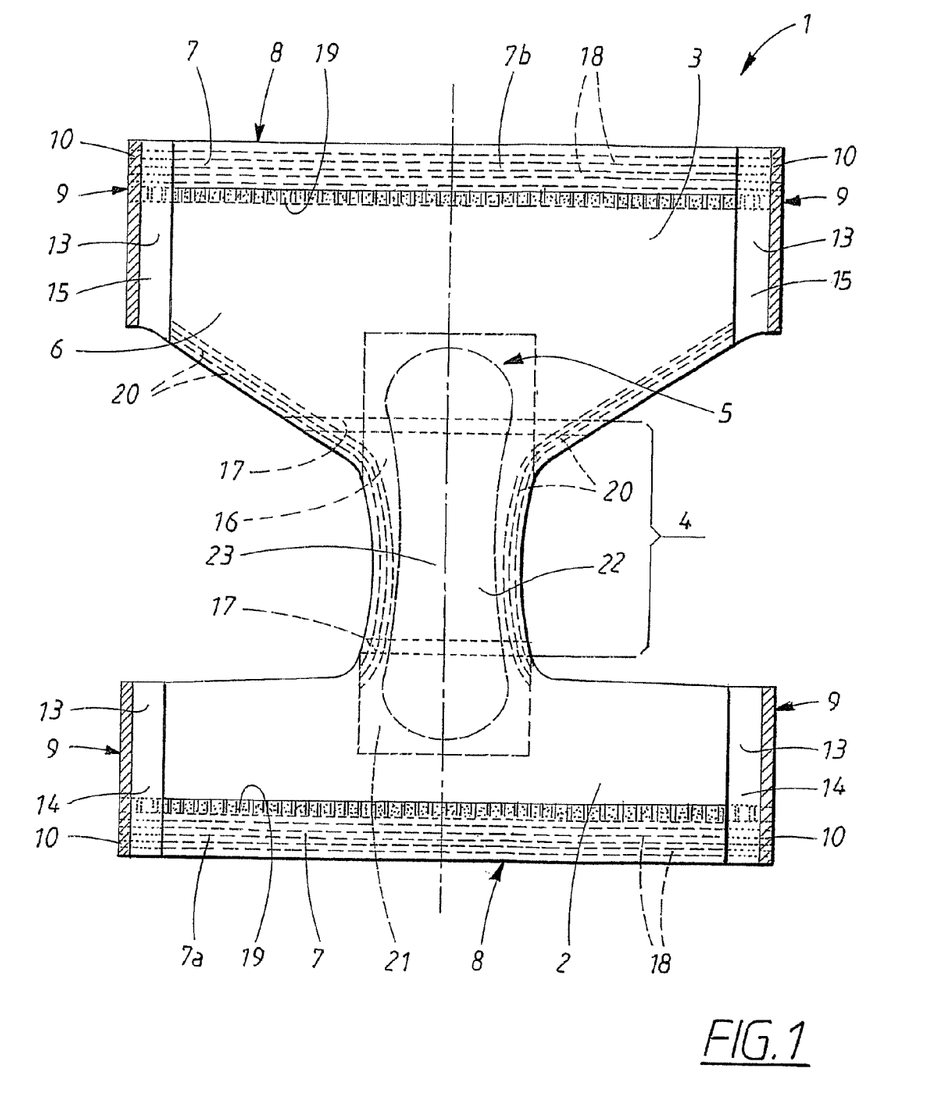
FIG. 1 shows a pant-type diaper in accordance with the invention in a flat state with opened side joins.
Figure 2:
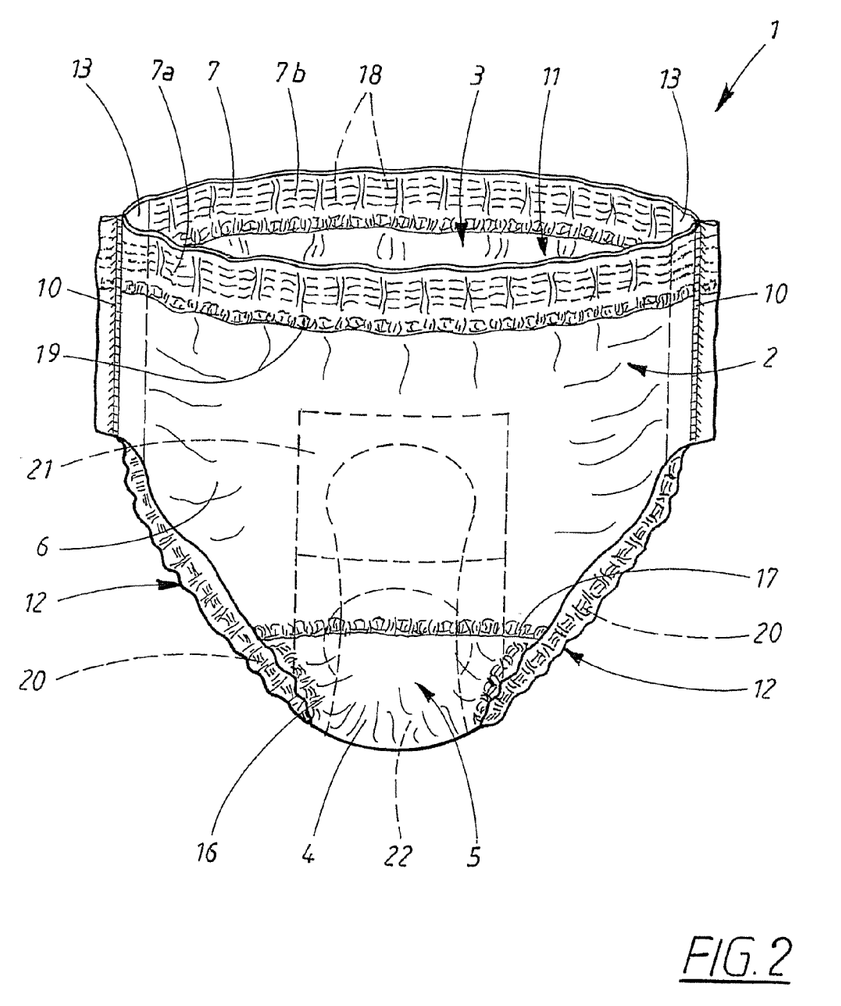
FIG. 2 shows the diaper in FIG. 3 with closed side joins.

The pant diaper 1 shown in FIGS. 1 and 2 is designed to enclose the lower part of a wearer's trunk like conventional underwear. In FIG. 1, the diaper 1 is shown from the inside, i.e. from the side facing the wearer when the article is being worn and in FIG. 2, the diaper 1 is shown from the outside, or the garment-facing side, which is the side that is facing away from the wearer when the diaper is worn.

The diaper 1 is shown in a flat state in FIG. 1, with opened side joins and with any pre-tensioned elastic components being stretched out. In FIG. 2, the diaper 1 is shown in a three-dimensional state as it will appear when it is being worn by a user.

The diaper 1 has a front panel 2, a back panel 3 and a crotch panel 4 extending between the front and back panels 2,3 and having a relatively narrow width as compared to the front and back panels 2,3. The front and back panels 2,3 are arranged to cover the wearer's hips and to extend over the belly and the back of the wearer to encircle the lower part of the wearer's trunk.

The diaper 1 further comprises a core region 5 extending from the crotch panel 4 into the front panel 2 and the back panel 3. The front and back panels 2,3 form part of a chassis 6 that extends on the garment-facing side of the diaper 1 and covers and surrounds the core region 5. The chassis 6 comprises the front panel 2, the back panel 3 the crotch panel 4 and an elastic waist band 7 secured to the front and back panels 2,3. Each of the front and back panels 2,3 has a waist edge 8, and a pair of side edges 9 respectively.

The term "panel" is used herein to denote a functional part of the diaper chassis while the terms "region" and "portion" are used to denote the location of a particular feature of the diaper, such as the core, in the chassis or to describe the intended positioning of a particular part of the diaper in relation to a user's body. A panel may be a separate component or an integral part of the chassis. A region or portion may fully or partially include one or more panels.

When components are joined, attached or secured to each other they are separate parts that have been bonded by any suitable means such as adhesively, by stitching or by ultrasonic welding or thermowelding. The term joined also includes separable joins, such as separable side joins and reclosable joins such as hook- and loop joins, reclosable tape joins, snap fasteners, etc. Components that are arranged on each other need not be bonded, although as used herein, the term "arranged" should be broadly interpreted to also include bonded components.

The front and back panels 2,3 are joined to each other along their side edges 9 in side seams 10, as shown in FIG. 2. The elastic waist band 7 consists of a front waist panel 7a and a back waist panel 7b, which are secured to the front panel 2 and the back panel 3, respectively. The front and back waist panels 7a, 7b are also joined to each other by means of the side seams 10. By joining the front and back panels 2, 3 and the waist panels 7a, 7b, the pant diaper 1 is provided with a waist opening 11 and a pair of leg openings 12.

The side seams 10 are made in accordance with the invention and include a connecting member 13. The connecting member 13 comprises weldable, thermoplastic material and has a first part 14 that is permanently secured along a side edge 9 on the inside of the front panel 2 and a second part 15 that is permanently secured along the corresponding side edge 9 on the inside of the back panel 3. The first and second parts 14,15 of each of the connecting members 13 are joined in the side seams 10 by thermowelding or ultrasonical welding.

FIG. 1 shows the diaper 1 in a flat state with the side seams 10 pulled apart and any elastic components that have been attached to the chassis 6 under tensional stress drawn out to the full dimensions of the chassis 6. FIG. 2 shows the pant diaper 1 as it appears when the side seams 10 are intact and any tensioned elastic elements have been allowed to relax and gather the chassis material to form elasticized leg and waist openings 11,12.

The front and back panels 2,3 are preferably constituted by an elastic web material such as an elastic laminate comprising layers of elastic film and nonwoven. The elastic laminate can be of the kind disclosed in International Patent Application No. WO 03/041988. Such a laminate is produced by incrementally stretching an elastic film layer between two non-elastic cloth-like layers. Incremental stretching is carried out by passing the laminate between intermeshing gear rollers.

Activation of elastic laminates by incremental stretching is also disclosed in U.S. Pat. Nos. 5,143,679, 5,156,793, 5,167, 897, 5,422,172, 5,592,690 5,634,216 and 5,861,074. The non-elastic cloth-like layers are fully or partially broken or torn during the activation process so that the elasticity of the laminate after activation is governed by the elasticity of the elastic film layer.

The front and back panels 2,3 are preferably elastically stretchable at least in the direction of the waist edges 8 but may also be elastically stretchable perpendicular to the waist edges 8, in the direction of the side edges 9.

The elastic film in the elastic laminate is preferably perforated in order to provide breathability in the laminate. This can be achieved directly in conjunction with the lamination process if, for instance, one or two nonwoven webs are bonded to the elastic film by means of extrusion coating. The perforating step can be carried out by passing the combined elastic layer and nonwoven material over a vacuum lamination drum while the elastic layer is in a molten or semi-molten state. Such a process is disclosed in U.S. Pat. No. 5,733,628 and results in the elastic film being formed into a three-dimensional apertured laminate layer.

The crotch panel 4 is formed from a crotch material 16 that has been joined to the front and back panels 2,3 at crotch seams 17. Hence, the crotch material 16 which can be a non-elastic material, such as a non-elastic nonwoven material, is arranged in the core region 5 of the article and overlaps slightly with the elastic front and back panels 2,3. The joining can be made in any suitable way such as by ultrasonic welding, adhesively or similar. Alternatively, an outer nonwoven material may extend continuously over the front and back panels 2, 3 and the crotch panel 4 so that no seams or joins 17 are needed between the panels 4,2,3.

In the shown example, the elastic waist band 7 comprises first and second plies of substantially non-elastic nonwoven material that is elasticized by one or more elongate elastic members 18, such as elastic threads or bands. The first and second plies can be formed from a single layer of material that is folded over onto itself or can be made from two separate strips of material. The elastic members 18 are arranged in the waist band 7 in a tensioned state such that they contract and gather the nonwoven material in the waist band 7 when they are allowed to relax, as shown in FIG. 2.

The elastic waist band 7 is secured to the front and back panels 2,3 with the elastic members 18 in an extended state and with the material in the front and back panels sandwiched between the nonwoven plies in the waist band. Alternatively, the elastic waist band 7 can be a component that is prefabricated and joined to the outside or the inside of the front and back panels 2,3 respectively. The waist band join 19 between the waist band 7 and the front and back panels 2,3 can be made in any suitable way such as by means of ultrasonic welding, heat welding, or adhesively. A further option is to create the waist band 7 from one or more non-elastic nonwoven layers that are also parts of the front and back panels 2,3 and form continuous extensions thereof. It is also conceivable to form an elastic waist feature by double-folding portions along the waist edges 8 of the elastic front and back panels 2,3 and optionally supplementing the folded portions by additional elastic elements.

Elastic members 20 are also arranged at the edges of the leg openings 12 and serve to elasticize the leg openings 12. The elastic members at the leg openings 12 can be any kind of conventional elastic elements such as elastic threads, bands, foam strips, or similar.

The planar extension of the core region 5 is defined by a liquid-impervious barrier sheet 21 arranged between an absorbent core 22 and the chassis 6. The liquid-impervious barrier sheet 21 has rectangular shape and the absorbent core 22 is hour-glass shaped. A liquid permeable topsheet 23 is arranged over the core 22 and the liquid-impervious barrier sheet 21. Hence, the liquid-impervious barrier sheet 21 underlies the absorbent core 22 and the adjacent areas immediately outside the absorbent core 22.

The liquid-permeable topsheet 23 can consist of any material known for the purpose, such as a layer of nonwoven material, a perforated plastic film, net material, tow, or the like. The topsheet 23 can, of course, also consist of a laminate of two or more sheets of the same or different material.

The liquid-impervious barrier sheet 21 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 21 is breathable, i.e. permits the passage of water vapour through the sheet 21.

The absorption core 22 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core 22 can comprise non-absorbent components such as stiffening elements, shaping elements, binders, etc. Various types of liquid-receiving porous structures such as fibre wads, open-cell foam or the like can also be included in the core.

The topsheet 23, barrier sheet 21 and absorption core 22 may have been produced as a separate component or "core pack" that has subsequently been integrated in the diaper chassis. The various components included in the core pack can be connected to one another in a conventional manner, for example by adhesive bonding, ultrasonic welding or thermowelding. The core pack can of course contain further components in addition to those described herein. The core pack may, for example, comprise a liquid transport sheet, elastic members, shape-stabilizing members, shaping elements or the like.

In addition to the components described in connection to the diaper in FIGS. 1 and 2, an absorbent pant-type article in accordance with the invention may comprise any other features and elements known in the art. Examples of such additional features are disposal means in the form of disposal tapes or pockets for keeping a used article in rolled-up or folded state, different kinds of barriers such as raised, elasticated side barriers, barrier sheets along the waist edges, etc. and also supplementary fastening elements that can be used to refasten an article that has been opened by tearing of the side seams.

Figure 3:
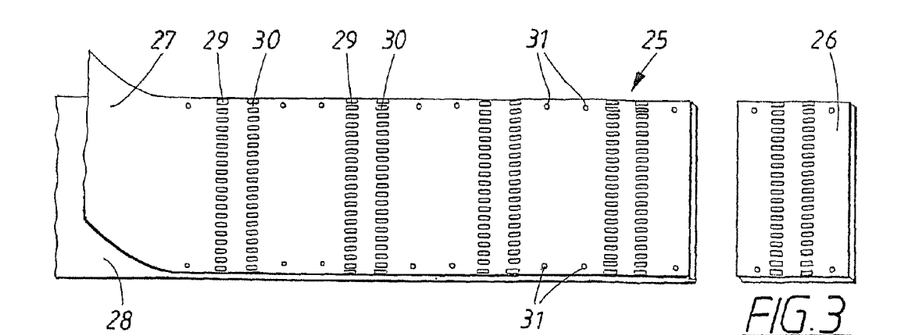
FIG. 3 shows a web of connecting member blanks.
Figure 6:
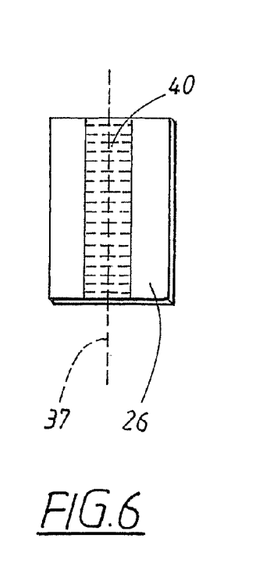
FIG. 6 shows an alternative embodiment of a connecting member blank.

FIG. 3 shows a continuous web 25 of connecting member blanks and a connecting member blank 26 that has been severed from the continuous web 25. The continuous web 25 is formed by joining two continuous webs 27,28 of weldable material in face-to-face relationship along paired weld lines 29,30 extending transversely across the web of connecting member blanks 26. In accordance with a further alternative embodiment of the invention, shown in FIG. 6, the weld lines can be combined into one weld line 40 having a width corresponding to the combined width of the individual weld lines 29,30 and the non-welded gap between the individual weld lines 29,30 shown in FIG. 3. The weld lines 29,30,40 can be made up of individual, discrete bonds as shown in FIGS. 3 and 6. Individual bonds may be in the form of spots, broken lines or other pattern elements arranged along the weld lines 29,30, 40. Alternatively, the weld lines can be continuous line bonds.

The individual connecting member blanks 26 are severed from the continuous web 25 of connecting member blanks by cutting the web 25 between each pair of weld lines 29,30 or between each broad weld line 40 to create individual connecting member blanks each containing a set of two individual weld lines 29,30 or a single broad weld line 40.

Figure 4:
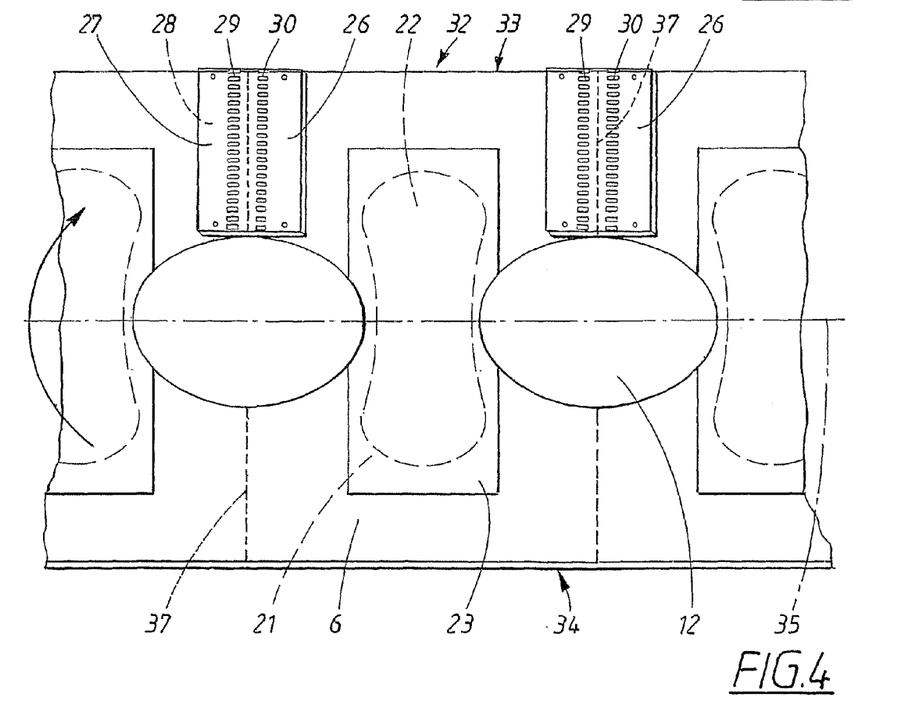
FIG. 4 shows pieces of connecting member blanks attached to a chassis web.

In the embodiment shown in FIGS. 3 and 4, the continuous web 25 of connecting member blanks has been provided with optional transport bonds, 31 in the form of small, weak point bonds arranged along the edges of the web 25. The transport bonds 31 keep the otherwise non-bonded portions of the layers 27,28 on either side of the weld lines 29, 30 from separating during the subsequent process steps. The transport bonds 31 are preferably formed concurrently with the bonds along the weld lines 29, 30 by thermobonding or ultrasonic bonding.

The individual connecting member blanks 26 are then introduced in a pant-forming process for forming a pant-type absorbent article and one of the layers 28 in each connecting member blank 26 is permanently or releasably secured to a chassis web 32 as shown in FIG. 4. The chassis web 32 is shown schematically in FIG. 4 with cutouts for leg openings 12 and boundaries between individual chassis structures 6 indicated by dotted lines 37. A core component including a core 22, a topsheet 23 and a backsheet 21 is shown to be placed between leg cutouts 12. The connecting member blanks 26 are secured at predetermined locations along a first edge 33 of the chassis web 32, corresponding to where the side seams 10 will be located in the finished pant-type absorbent article. The connecting member blanks 26 are secured with the weld lines 29,30 or 40 arranged in the transverse direction of the chassis web 32. The connecting member blanks 26 may be secured to the chassis web 32 either before or after the leg cutouts 12 have been formed in the web 12. Furthermore, the leg cutouts 12 may be formed while the web 12 is in the state shown in FIG. 4 or may be formed later in the pant-forming process after the chassis web 32 has been folded along a longitudinal folding line 35. If the connecting member blanks 26 are joined to the chassis web 32 before forming the leg cutouts 12, the leg cutouts may be partially made through a part of the connecting member blanks 26.

Securement is preferably achieved by means of adhesive, such as thermoplastic hotmelt adhesive or latex. However, it is conceivable to use other types of securement, such as thermowelding, ultrasonic welding or stitching. The securement may be permanent or may be made to allow openability. The bond between the chassis web 32 and each connecting member blank 26 occupies a comparatively large area offering a strong, secure bond. During normal use of the pant-type article the bond will only be exposed to shearing stress between the material in the chassis web and the connecting member.

After the connecting member blanks 26 have been secured to the first edge of the chassis web 32, the chassis web 32 is folded along a longitudinal folding line 35 to bring a second edge 34 of the chassis web 32 in alignment with the first edge 33 of the chassis web 32 and to cover the connecting member blanks 26.

The chassis web 32 is then permanently or releasably secured to the other layer 27 of the connecting member blanks 26 along the second edge 34 of the chassis web 32.

Finally, the folded, assembled chassis web 32 is severed in the transverse direction along the line 37 between the weld lines 29,30 in the connecting member blanks 26 to separate individual pant-type articles from the chassis web 32. In the embodiment where the connecting member blanks 26 each contain a single broad weld line 40, the individual pant-type articles are formed by cutting the web in the weld line 40, preferably centrally in the weld line 40 along line 37 as shown in FIG. 6.

The production process may, of course comprise further steps, such as the application of waist elastic, application of leg elastic, barrier elastic, etc. For pant-type absorbent articles, waist elastic may be continuously applied to the chassis web in the form a pre-formed elastic waistband or as continuous or discontinuous elastic members applied to a chassis component at one or both edges 32,33 of the chassis web 32. The waist elastic may be applied to the chassis web 32 before or after the connecting member blanks have been joined to the web.

In the finished pant-type absorbent article, each weld line 29,30 or each part of a combined, broader weld line 40 forms a side seam 10. Hence, the invention provides a means of pre-fabricating side seams and incorporating the prefabricated side seams in a pant-type absorbent article. This is a considerable advantage in the pant-forming process since the welding step is a comparatively slow process step that limits the production speed. By producing the connecting member blanks 26 separately, the connecting member blanks 26 may subsequently be introduced in the pant-forming process at a much higher speed than would otherwise have been possible. Each connecting member blank 26 forms two connecting members 13 that are incorporated in side seams in consecutive absorbent articles that are cut or severed from a chassis web.

Figure 5:
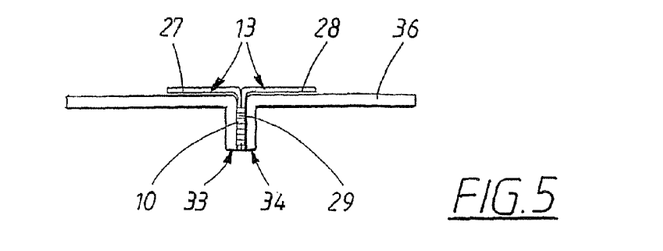
FIG. 5 shows a detail of a side join in a pant-type article

FIG. 5 shows a side seam 10 with a side edge portion of a chassis structure 36 and a connecting member 13. The side seam 10 is formed by means of a bonding technique resulting in a bond that has sufficient strength to withstand any stress induced by normal use of the absorbent article and that preferably can be peeled open or torn in a controlled manner when the article is being removed from the wearer. By choosing a material having high thermoplastic content for the connecting member, it is possible to use thermowelding techniques to obtain a bond having the requisite peel strength but where the peel strength can be controlled to allow the bond to be manually opened.

The connecting member may consist of or include a thermoplastic film but is preferably made of a non-elastic fibrous nonwoven web comprising thermoplastic fibres. Examples of suitable thermoplastic polymers for use in the nonwoven webs and thermoplastic films are polyethylene, polyesters, polypropylene and other polyolefin homopolymers and copolymers. Particularly well suited nonwoven webs are those comprising thermoplastic fibres that are a blend of polypropylene and polyethylene fibres. The weldable nonwoven webs have a high content of thermoplastic fibres and contain at least 50% thermoplastic fibres and preferably at least 80% thermoplastic fibres.

Description of Test Methods

Elasticity Test

The method measures how an elastic material behaves at cycles of repeated load and unload. The sample is stretched to a predetermined elongation and cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is placed in the clamps according to the marks and it is made sure that the sample is centred and fastened perpendicularly in the clamps. The tensile tester is started and three cycles between 0 and the predetermined elongation equal to the highest defined $1^{st}$ load are performed. Before the last cycle, the sample is relaxed for 1 minute, and then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material is a material that has a permanent elongation after relaxation of more than 10% after having been subjected to an elongation of 30%.

Tensile Strength, Side Joins

The tensile strength of the side joins is measured according to the method (reference ASTM D 882).

Figure 7:
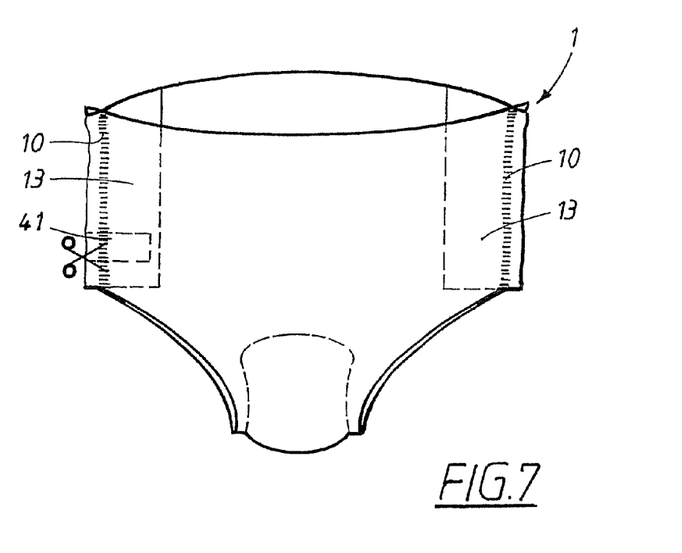
FIGS. 7-9 show, schematically, a method for measuring the strength of the side joins in a pant-type article according to the present invention.
Figure 8:
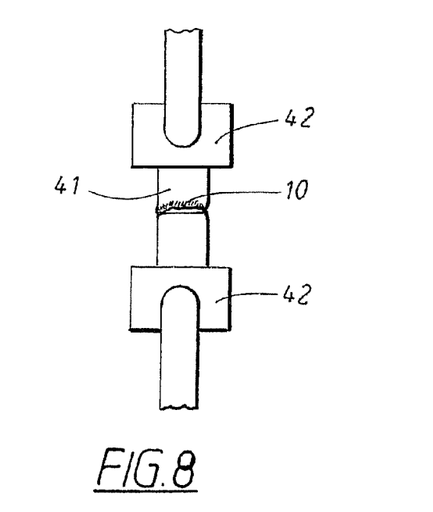
Figure 9:
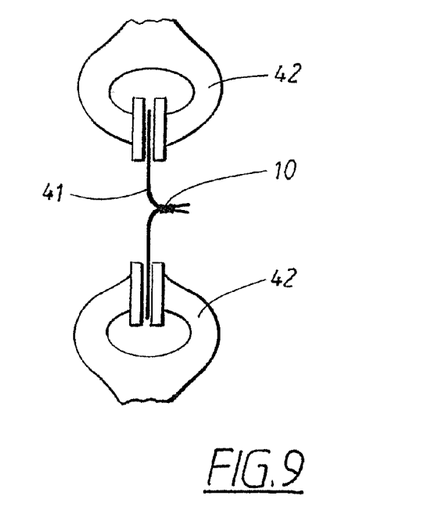

Apparatus:
   A tensile tester connected to a computer
   Crosshead speed—500 mm/min
   Clamp distance—50 mm
   A sample cutter or cutting tool, accuracy ±0.1 mm Sample Preparation:

Test specimens 41 are cut from the pant-type absorbent article 1, as shown in FIG. 7, in areas which are provided with a connecting member 13 in accordance with the invention. The width of the test specimens 41 will be 25.4 mm and the length if possible 50 mm longer than the distance between the clamps on the tensile test instrument Instron 4301. FIGS. 8 and 9 show how the test specimens 41 are secured in the clamps 42.

It should be checked that the cutter blade is undamaged since it is of importance that the edges of the sample are even and without break notches.

The samples are conditioned at least 4 h in 50% RH±5% RH and 23° C.±1° C. before testing.

Procedure:

The tensile tester is calibrated according to the apparatus instruction and set to zero. The material is prevented from slipping by using clamps covered with galloon or similar material. The sample is mounted in the clamps and it is ensured that it is not obliquely or unevenly fastened and the tensile tester is started. The tensile tester is started, and stopped after the material has broken (if not automatically controlled). Test specimens which fail prematurely, such as by breaking at the clamps or from being damaged in sample preparation should be ignored, if possible.

The following results are expressed by the tensile tester/computer:
   Maximum force, N/25.4 mm
   Elongation at maximum force, %
   Break force, N/25.4 mm
   Elongation at break force, %
   Knee point, N/%

The tensile strength of each side join is recorded as the force required to break the join.

The tensile strength of the side joins, in a direction transverse to the side seams 10, should preferably exceed 5 N/25.4 mm, more preferably the minimum tensile strength exceeds 10 N/25.4 mm or 12 N125.4 mm and can be on average at least 15 N/25.4 mm or 20 N/25.4 mm, where the breaking strength of the cover materials in the pant-type absorbent article in the transverse direction preferably exceeds the tensile strength for the side seams provided in the connecting member 10 and the joins between the connecting member and the material in the front and back panels of the article.

The invention claimed is:

1. A method for producing a pant-type pant absorbent article, each article including a chassis structure comprising a front panel having a front end edge and first and second side edges, a back panel having a back end edge and first and second side edges and a crotch panel arranged between the front and back panels, said chassis structure having an integrated absorbent core component,
   the method including a pant-forming process comprising forming the chassis structure and joining the first and second side edges of the front panel to the corresponding first and second side edges of the back panel, and incorporating the absorbent core component into the chassis structure,
   wherein the pant-forming process comprises:
   a) producing a continuous web of connecting member blanks by joining two continuous webs of weldable material in direct face-to-face relationship along paired weld lines extending transversely across the web of connecting member blanks;
   b) severing the web of connecting member blanks between each pair of weld lines to create individual connecting member blanks;
   c) securing said individual connecting member blanks to a chassis web at predetermined locations along a first edge of said chassis web with said weld lines arranged in the transverse direction of the chassis web;
   d) folding said chassis web along a longitudinal folding line to bring a second edge of said chassis web in alignment with said first edge of said chassis web;
   e) securing said chassis web to said connecting member blanks along said second edge of said chassis web;
   f) severing said chassis web between said weld lines in said connecting member blanks to separate individual pant-type articles from said chassis web,
   wherein said connecting member blanks are permanently secured to said chassis web in step c) and/or in step e).

2. A method for producing a pant-type pant absorbent article, each article including a chassis structure comprising a front panel having a front end edge and first and second side edges, a back panel having a back end edge and first and second side edges and a crotch panel arranged between the front and back panels said chassis structure having an integrated absorbent core component,
   the method including a pant-forming process comprising forming the chassis structure and joining the first and second side edges of the front panel to the corresponding first and second side edges of the back panel, and incorporating the absorbent core component into the chassis structure,
   wherein the pant-forming process comprises:
   a) producing a continuous web of connecting member blanks by joining two continuous webs of weldable material in direct face-to-face relationship along a single weld line extending transversely across the web of connecting member blanks;
   b) severing the web of connecting member blanks between each single weld line to create individual connecting member blanks;
   c) securing said individual connecting member blanks to a chassis web at predetermined locations along a first edge of said chassis web with said weld line arranged in the transverse direction of the chassis web;
   d) folding said chassis web along a longitudinal folding line to bring a second edge of said chassis web in alignment with said first edge of said chassis web;
   e) securing said chassis web to said connecting member blanks along said second edge of said chassis web;
   f) severing said chassis web in said weld line in said connecting member blanks to separate individual pant-type articles from said chassis web,
   wherein said connecting member blanks are permanently secured to said chassis web in step c) and/or in step e).

3. The method according to claim 1, wherein the permanent securement is made by adhesive.

4. The method according to claim 1, wherein the continuous web of connecting member blanks comprises a thermoplastic film.

5. The method according to claim 1, wherein the continuous web of connecting member blanks comprises a thermoplastic nonwoven web.

6. The method according to claim 4, wherein the continuous web of connecting member blanks contains at least 50% thermoplastic polymeric material.

7. The pant-type pant absorbent article produced according to the method in claim 1, comprising a chassis structure comprising a front panel having a front end edge and first and second side edges, a back panel having a back end edge and first and second side edges and a crotch panel arranged between the front and back panels at least one of said front and back panels comprising an elastic nonwoven/film laminate, and a core being integrated with the chassis structure, the first and second side edges of the front panel being joined by side seams to the corresponding first and second side edges of the back panel, wherein each said side seam comprises a thermowelded join formed in a weldable connecting member, the connecting member comprising a first part being secured to a side edge on the front panel and a second part being secured to a corresponding side edge on the back panel, said first and second parts of said connecting member being joined by said thermowelded join, said connecting member is permanently secured to the front and back panels.

8. The pant-type pant absorbent article according to claim 7, wherein the connecting member is secured to the front and back panels by means of an adhesive.

9. The pant-type absorbent article according to claim 7, wherein the side seams are openable side seams.

10. The pant-type absorbent article according to claim 7, wherein the connecting member comprises a thermoplastic film.

11. The pant-type absorbent article according to claim 7, wherein the connecting member comprises a thermoplastic nonwoven web.

12. The pant-type absorbent article according to claim 7, wherein the connecting member contains at least 50% thermoplastic polymeric material.

13. The pant-type absorbent article according to claim 7, wherein the connecting member is a rectangular piece of material having a welded join running across the piece of material, and forming the side seam on the pant-type absorbent article.

14. The pant-type absorbent article according to claim 13, wherein the connecting member has a width perpendicular to the side seam of 20-200 mm.

15. The pant-type absorbent article according to claim 13, wherein the connecting member has a length parallel to the side seam corresponding to at least 25% of the length of the side seam.

16. The pant-type absorbent article according to claim 7, wherein an elastic waist panel is arranged on at least one of the front and back panels.

17. The pant-type absorbent article according to claim 16, wherein the elastic waist panel extends continuously all the way between the side seams.

18. A pant-type absorbent article according to claim 7, wherein the absorption core is part of a core component comprising a topsheet, a barrier sheet and the absorption core arranged between the topsheet and the barrier sheet.

19. The method according to claim 2, wherein the permanent securement is made by adhesive.

20. The method according to claim 2, wherein the continuous web of connecting member blanks comprises a thermoplastic film.

21. The method according to claim 2, wherein the continuous web of connecting member blanks comprises a thermoplastic nonwoven web.

22. The method according to claim 20, wherein the continuous web of connecting member blanks contains at least 50% thermoplastic polymeric material.

23. The pant absorbent article produced according to the method in claim 2, comprising a chassis structure comprising a front panel having a front end edge and first and second side edges, a back panel having a back end edge and first and second side edges and a crotch panel arranged between the front and back panels at least one of said front and back panels comprising elastic nonwoven/film laminate, and a core being integrated with the chassis structure, the first and second side edges of the front panel being joined by side seams to the corresponding first and second side edges of the back panel, wherein each said side seam comprises a thermowelded join formed in a weldable connecting member, the connecting member comprising a first part being secured to a side edge on the front panel and a second part being secured to a corresponding side edge on the back panel, said first and second parts of said connecting member being joined by said thermowelded join, said connecting member is permanently secured to the front and back panels.

24. The pant absorbent article according to claim 23, wherein the connecting member is secured to the front and back panels by means of an adhesive.

25. The pant-type absorbent article according to claim 23, wherein the side seams are openable side seams.

26. The pant-type absorbent article according to claim 23, wherein the connecting member comprises a thermoplastic film.

27. The pant-type absorbent article according to claim 23, wherein the connecting member comprises a thermoplastic nonwoven web.

28. A pant-type absorbent article according to claim 23, wherein the absorption core is part of a core component comprising a topsheet, a barrier sheet and the absorption core arranged between the topsheet and the barrier sheet.

* * * * *